United States Patent
Kang et al.

(10) Patent No.: US 10,588,910 B2
(45) Date of Patent: Mar. 17, 2020

(54) PHARMACEUTICAL COMPOSITION COMPRISING EPIDITHIODIOXOPIPERAZINE COMPOUND OR DERIVATIVE THEREOF, OR PHARMACEUTICALLY ACCEPTABLE SALT THEREOF, FOR PREVENTING OR TREATING PULMONARY HYPERTENSION

(71) Applicant: VASTHERA CO. LTD., Seoul (KR)

(72) Inventors: Sang Won Kang, Seoul (KR); Ki Hwan Kwon, Seoul (KR)

(73) Assignee: Vasthera Co. Ltd., Seoul (KR)

( * ) Notice: Subject to any disclaimer, the term of this patent is extended or adjusted under 35 U.S.C. 154(b) by 0 days.

(21) Appl. No.: 16/315,536

(22) PCT Filed: Jul. 5, 2017

(86) PCT No.: PCT/KR2017/007191
§ 371 (c)(1),
(2) Date: Jan. 4, 2019

(87) PCT Pub. No.: WO2018/008984
PCT Pub. Date: Jan. 11, 2018

(65) Prior Publication Data
US 2019/0298732 A1  Oct. 3, 2019

(30) Foreign Application Priority Data

Jul. 5, 2016 (KR) .................. 10-2016-0085040

(51) Int. Cl.
*A61K 31/548* (2006.01)
*A61P 9/12* (2006.01)
*A61K 31/407* (2006.01)
*C07D 513/08* (2006.01)
*A61K 31/549* (2006.01)

(52) U.S. Cl.
CPC .......... *A61K 31/548* (2013.01); *A61K 31/407* (2013.01); *A61K 31/549* (2013.01); *A61P 9/12* (2018.01); *C07D 513/08* (2013.01)

(58) Field of Classification Search
CPC .. A61K 31/548; A61K 31/407; A61K 31/549; A61P 9/12; C07D 513/08
USPC ....................................................... 514/222.8
See application file for complete search history.

(56) References Cited

U.S. PATENT DOCUMENTS

2014/0112940 A1  4/2014  Lane

FOREIGN PATENT DOCUMENTS

| KR | 10-2014-0138545 A | 12/2014 |
| WO | WO 02/076939 A2 | 10/2002 |
| WO | WO 2008/008033 A1 | 1/2008 |
| WO | WO 2010/033879 A2 | 3/2010 |
| WO | WO 2014/189343 A1 | 11/2014 |

OTHER PUBLICATIONS

Ernst-Russell et al., "Structure Revision and Cytotoxic Activity of the Scabrosin Esters, Epidithiopiperazinediones from the Lichen *Xanthoparmelia scabrosa*," *Australian Journal of Chemistry* 52(4): 279-283, 1999, abstract only.
Joshi et al., New Verticillin and Glisoprenin Analogues from *Gliocladium catenulatum*, a Mycoparasite of *Aspergillus flavus* Sclerotia, *J. Nat. Prod.* 62: 730-733, 1999.
Kleinwächter et al., "Epicorazine C, an Antimicrobial Metabolite from *Stereum hirsutum* HKI 0195," *The Journal of Antibiotics* 54(6): 521-525, Jun. 2001.
Moerman et al., "Evidence that the lichen-derived scabrosin esters target mitochondrial ATP synthase in P388D1 cells," *Toxicology and Applied Pharmacology* 190: 232-240, 2003.
Son et al., "New Cytotoxic Epidithiodioxopiperazines Related to Verticillin A From A Marine Isolate of the Fungus *Penicillium*," *Natural Product Letters* 13(3): 213-222, 1999, 11 pages.

*Primary Examiner* — Kristin A Vajda
(74) *Attorney, Agent, or Firm* — Seed IP Law Group LLP

(57) ABSTRACT

The present invention relates to a pharmaceutical composition for preventing or treating pulmonary arterial hypertension, which comprises an epidithiodioxopiperazine (ETP) compound or a derivative thereof, or a pharmaceutically acceptable salt thereof.

8 Claims, 9 Drawing Sheets

PHARMACEUTICAL COMPOSITION COMPRISING EPIDITHIODIOXOPIPERAZINE COMPOUND OR DERIVATIVE THEREOF, OR PHARMACEUTICALLY ACCEPTABLE SALT THEREOF, FOR PREVENTING OR TREATING PULMONARY HYPERTENSION

TECHNICAL FIELD

The present invention relates to a pharmaceutical composition for preventing or treating pulmonary arterial hypertension, comprising an epidithiodioxopiperazine (ETP) compound or a derivative thereof, or a pharmaceutically acceptable salt thereof.

BACKGROUND ART

The pulmonary artery is an artery that carries blood in the body from the right ventricle to the lungs in order to supply oxygen, and pulmonary arterial hypertension is defined as when the mean pulmonary artery pressure at rest is 25 mmHg or greater or when the mean pulmonary artery pressure during exercise is 30 mmHg. Pulmonary arterial hypertension is classified into “primary pulmonary arterial hypertension”, which is the case where no specific cause has been disclosed, and specific disease “associated pulmonary arterial hypertension”, which occurs secondarily due to a specific causative disease. Examples of the latter case include familial pulmonary arterial hypertension related to heredity, and the specific disease-associated pulmonary arterial hypertension may be caused by collagen vascular diseases (e.g., systemic sclerosis, systemic lupus erythematosus, etc.), portal hypertension, HIV infection, congenital heart diseases, and drugs or toxins such as an appetite suppressant or cocaine. Specific disease-associated pulmonary arterial hypertension is not significantly different from primary pulmonary arterial hypertension in terms of spontaneous progression, histopathological findings, response to treatment, etc. Primary pulmonary arterial hypertension is 1.7 times more common in women than in men and may occur in all ages, but it is frequent in those in their 20s and 30s. Approximately 7% of patients have a family history of mutation in the gene called BMPR2, by which the autosomal dominant trait appears to be inherited.

Patients with pulmonary arterial hypertension may present with symptoms such as shortness of breath (dyspnea), fainting, dizziness, peripheral edema (e.g., lower extremity edema), impotent feeling, anepithymia, increased heart rate, headache, precordialgia, cyanoderma, etc. Further, it may be accompanied by Raynaud’s phenomenon, in which the fingers and toes easily become cold and turn blue. Patients with pulmonary arterial hypertension are often initially exposed to misdiagnosis such as influences from asthma or excessive stress, resulting in breathing difficulties; and after an average of 2.5 years, the patients are diagnosed correctly.

For the treatment of pulmonary arterial hypertension, surgical intervention such as interventional atrial septostomy, lung transplantation, heart-lung transplantation, etc. can be performed, but drug treatment is preferred because of the high cost and risk of surgical intervention. Currently, there are methods to use a general vasodilator as a drug for treating pulmonary arterial hypertension, but most vasodilators are calcium channel blockers, which are difficult to apply because they often do not show a significant effect on pulmonary arterial hypertension and have side effects associated with administration. Therefore, it is necessary to discover an effective therapeutic agent for pulmonary arterial hypertension.

DISCLOSURE

Technical Problem

The present inventors have confirmed that an epidithiodioxopiperazine compound or a derivative thereof, which has an intramolecular disulfide bond in an epidithiodioxopiperazine ring, alleviates the symptoms of pulmonary arterial hypertension in an experimental animal model, thereby completing the present invention.

Technical Solution

The present invention provides a pharmaceutical composition for preventing or treating pulmonary arterial hypertension, comprising an epidithiodioxopiperazine compound or a derivative thereof, or a pharmaceutically acceptable salt thereof, which has an intramolecular disulfide bond in an epidithiodioxopiperazine ring.

Advantageous Effects

The pharmaceutical composition of the present invention, which comprises an epidithiodioxopiperazine (ETP) compound or a derivative thereof, can prevent or treat pulmonary arterial hypertension by effectively blocking thickening of the pulmonary arterial wall in a rat model in which pulmonary arterial hypertension is induced by MCT, and thus can prevent the heart, especially the right ventricle, from becoming hypertrophied.

BRIEF DESCRIPTION OF DRAWINGS

FIG. 1 is a diagram comparing the morphology and size of the entire hearts and right ventricles excised from the control group, monocrotaline (MCT) administration group, and dose-dependent chaetocin administration experimental groups.

FIG. 2 is a diagram showing the representative result obtained by H&E staining of the control group, that is, a heart excised from a rat in which pulmonary arterial hypertension is not induced.

FIG. 3 is an enlarged view showing the results of H&E staining of the control group, that is, a heart excised from a rat in which pulmonary arterial hypertension is not induced.

FIG. 4 is a diagram showing the representative result obtained by H&E staining of a heart excised from a rat, in which pulmonary arterial hypertension is induced by administering MCT.

FIG. 5 is an enlarged view showing the results of H&E staining of a heart excised from a rat, in which pulmonary arterial hypertension is induced by administering MCT.

FIG. 6 is a diagram showing the result of H&E staining of a heart excised from the experimental group in which 30 μg of chaetocin is administered to a rat, in which pulmonary arterial hypertension is induced by administering MCT.

FIG. 7 is an enlarged view showing the results of H&E staining of a heart excised from the experimental group in which 30 μg of chaetocin is administered to a rat, in which pulmonary arterial hypertension is induced by administering MCT.

FIG. 8 is a diagram showing the result of H&E staining of a heart excised from the experimental group in which 12

μg of chaetocin is administered to a rat, in which pulmonary arterial hypertension is induced by administering MCT.

BEST MODE FOR CARRYING OUT THE INVENTION

Figure 1:
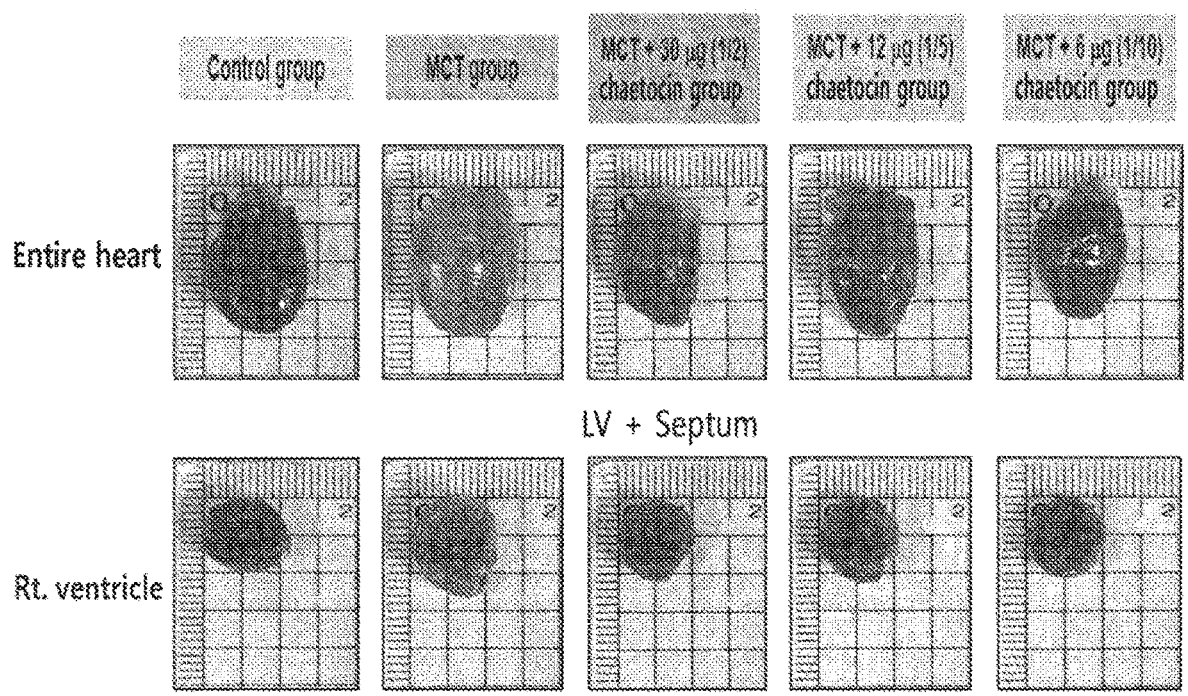
Figure 2:
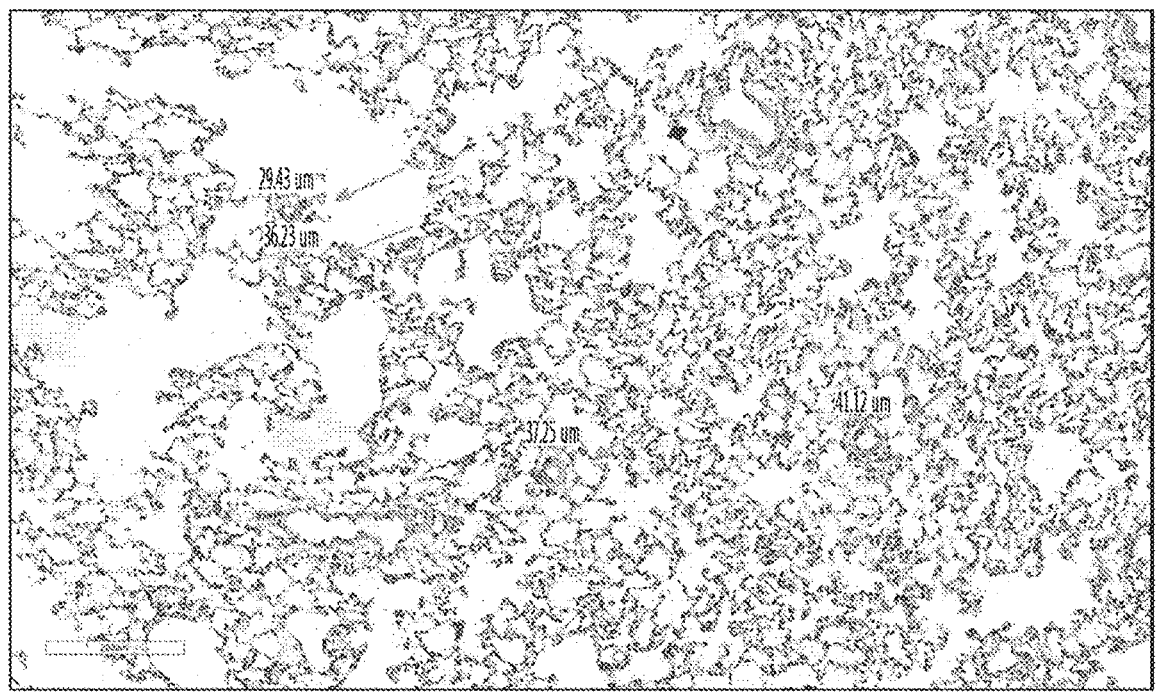
Figure 3:
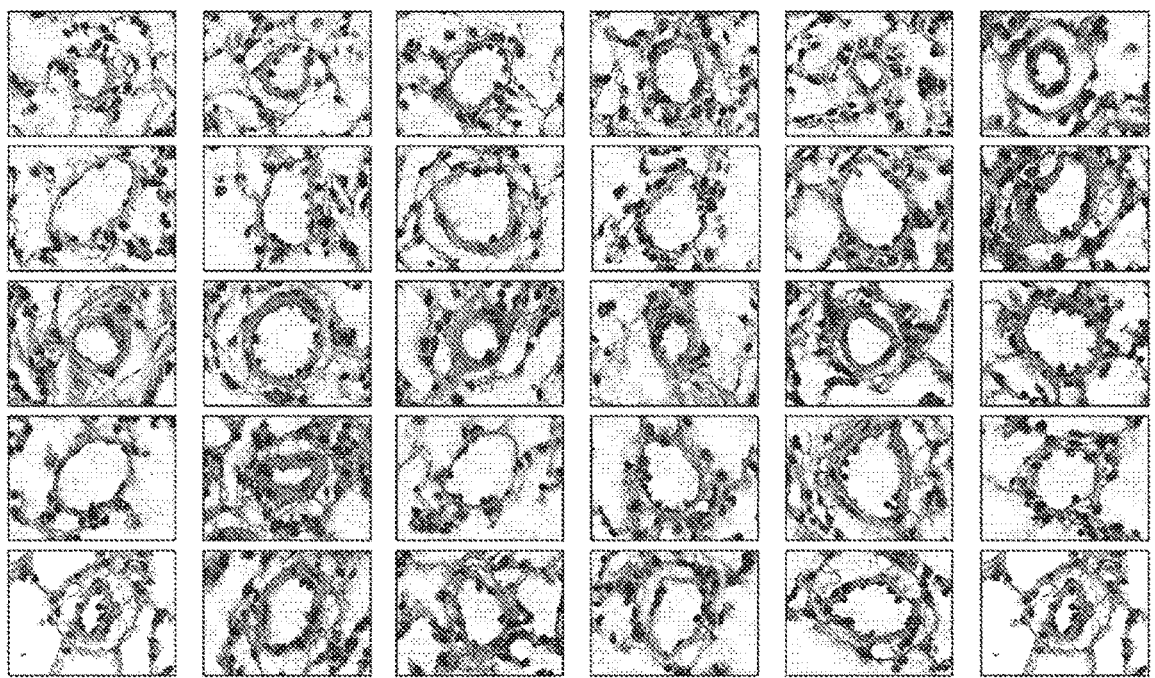
Figure 4:
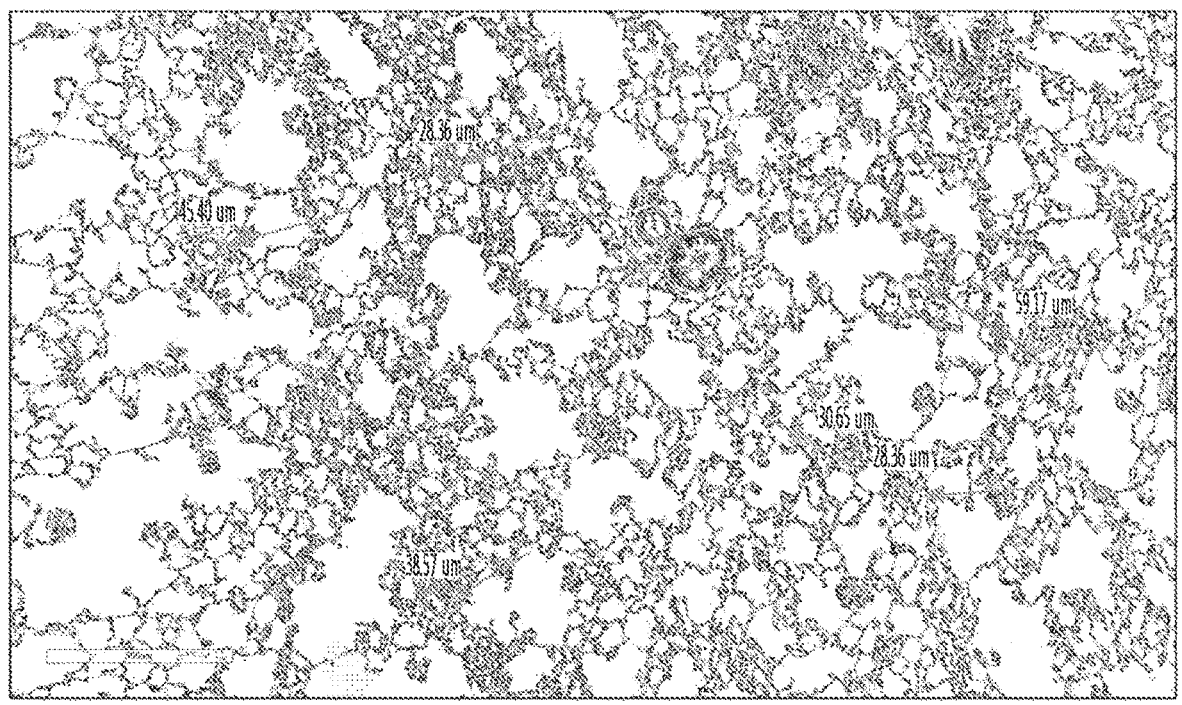
Figure 5:
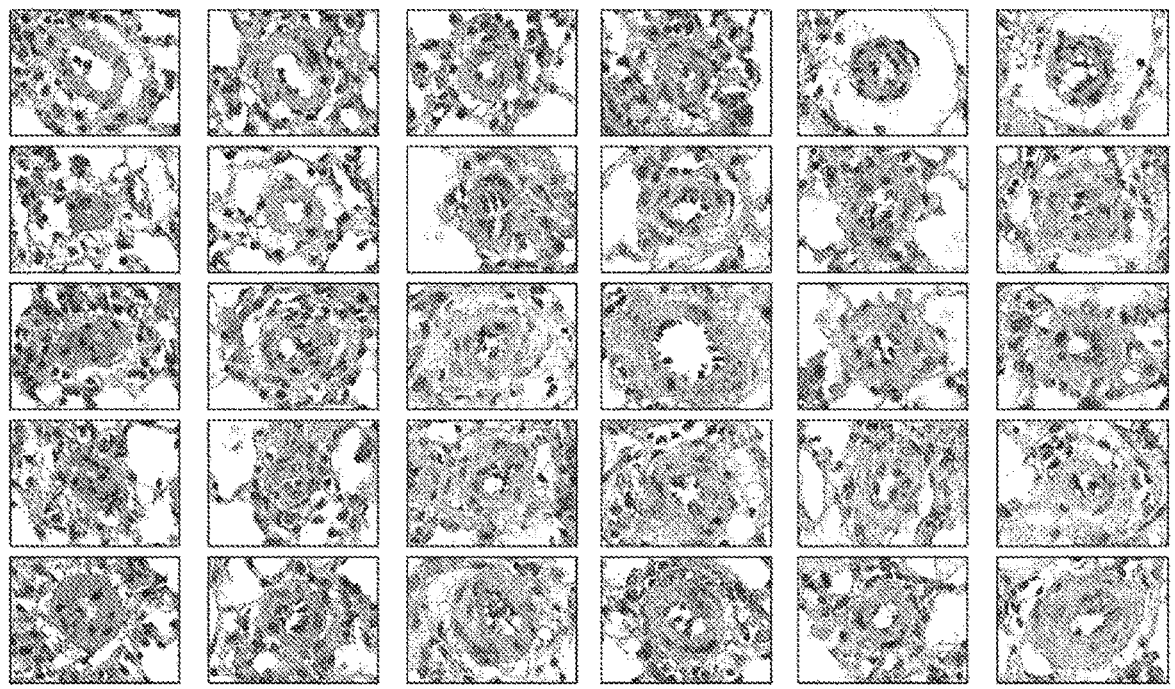
Figure 6:
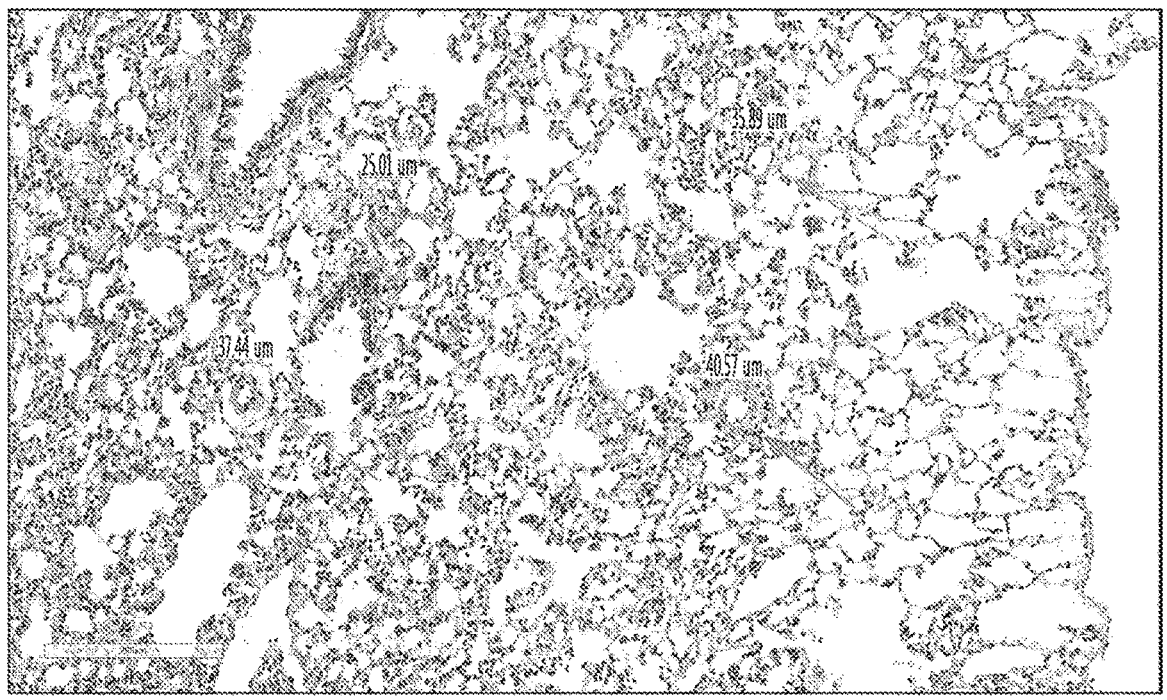
Figure 7:
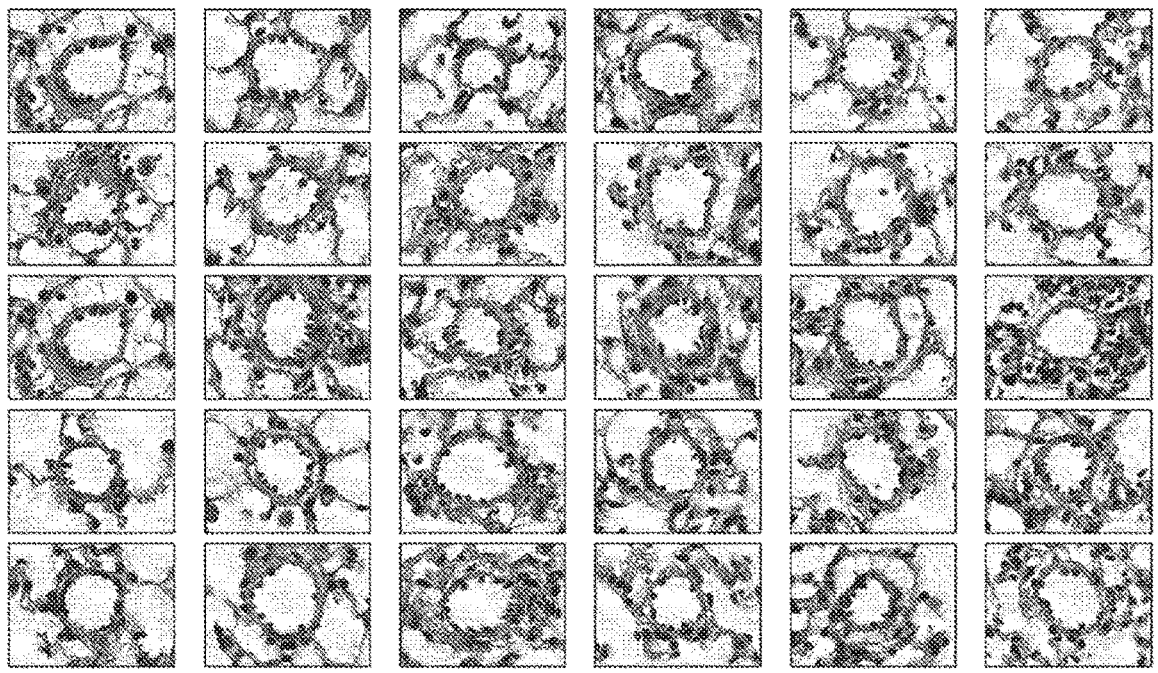
Figure 8:
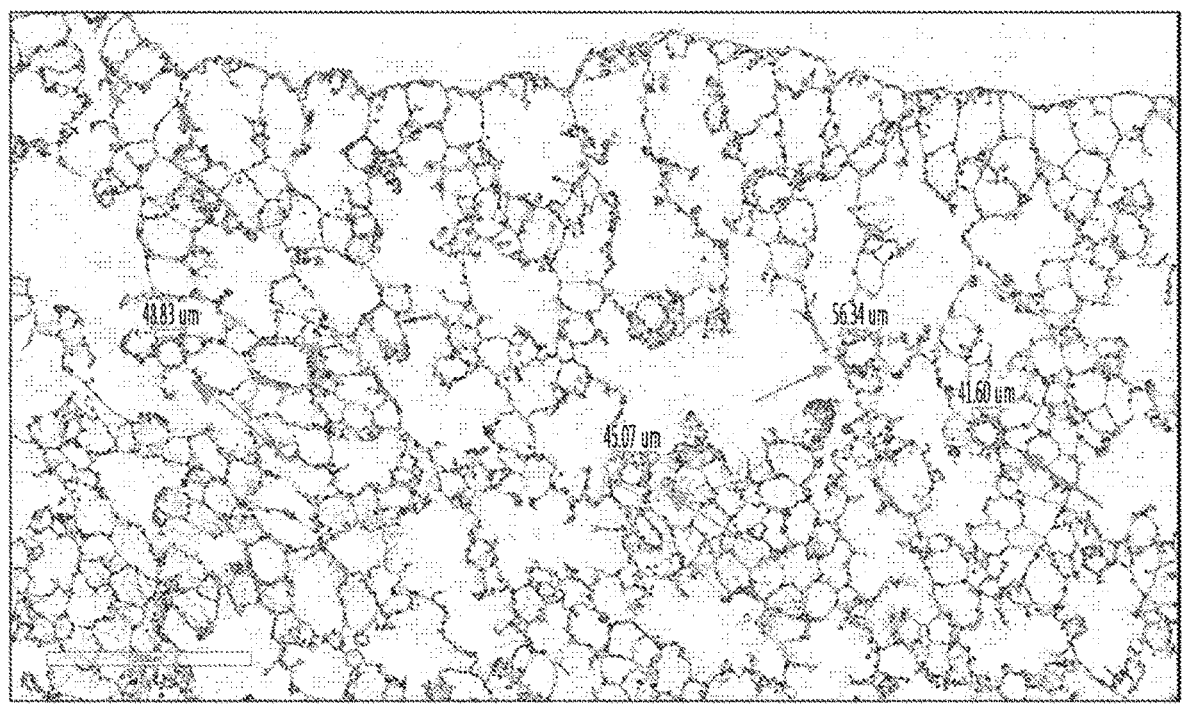
Figure 9:
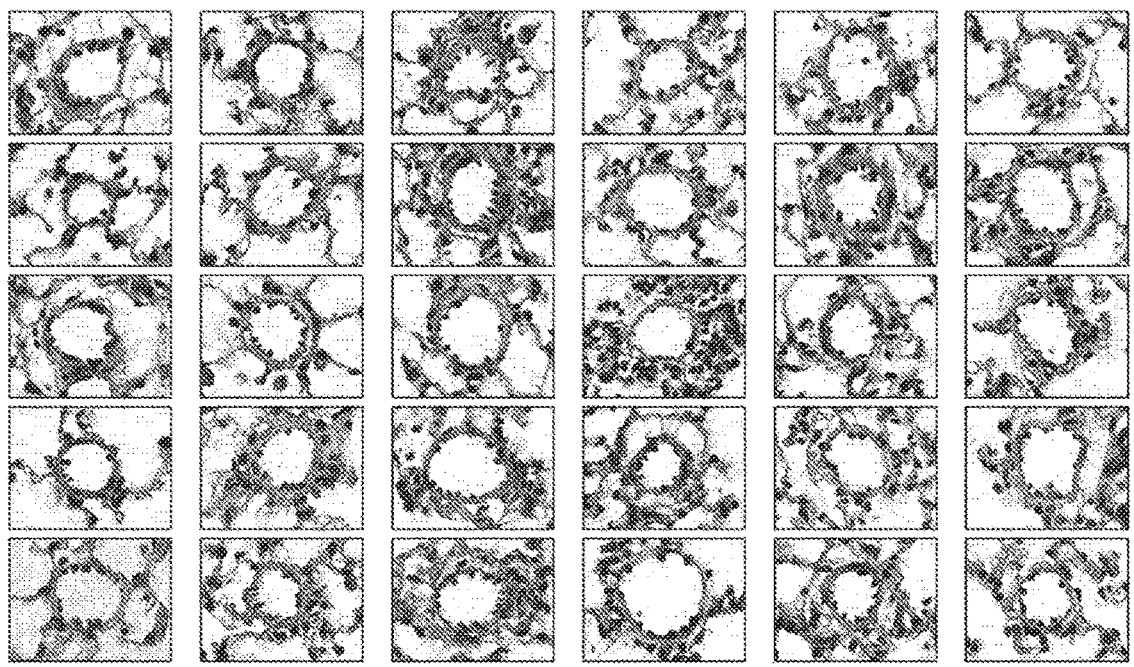
FIG. 9 is a diagram showing the result of H&E staining of a heart excised from the experimental group in which 12 μg of chaetocin is administered to a rat, in which pulmonary arterial hypertension is induced by administering MCT.
Figure 10:
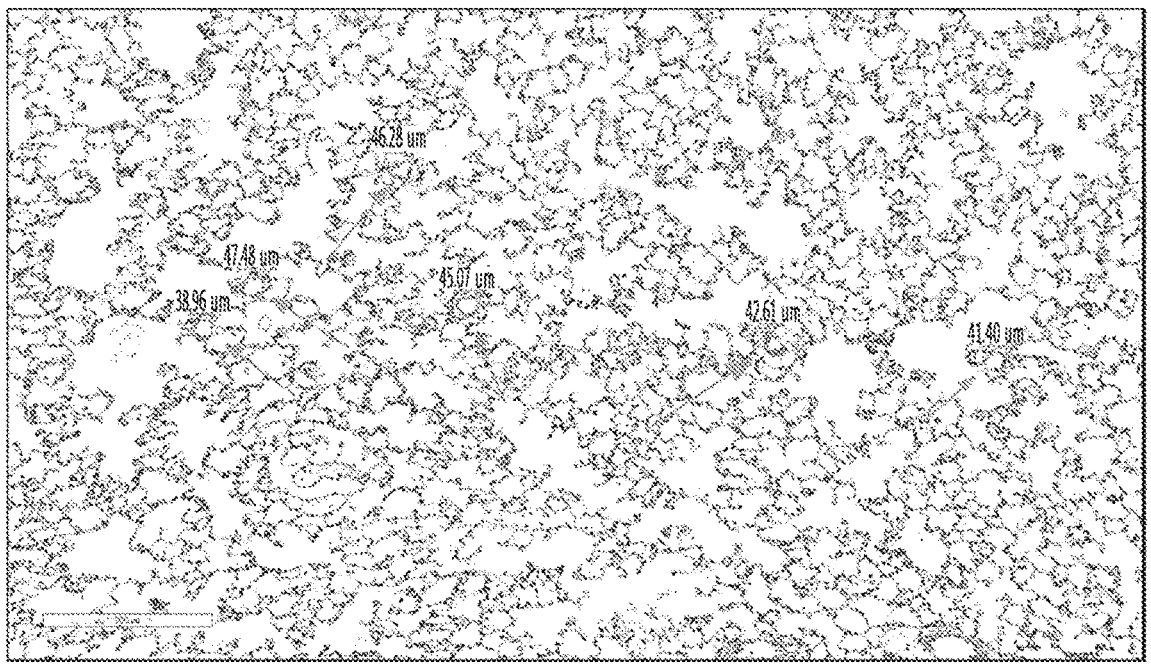
FIG. 10 is a diagram showing the result of H&E staining of a heart excised from the experimental group in which 6 μg of chaetocin is administered to a rat, in which pulmonary arterial hypertension is induced by administering MCT.
Figure 11:
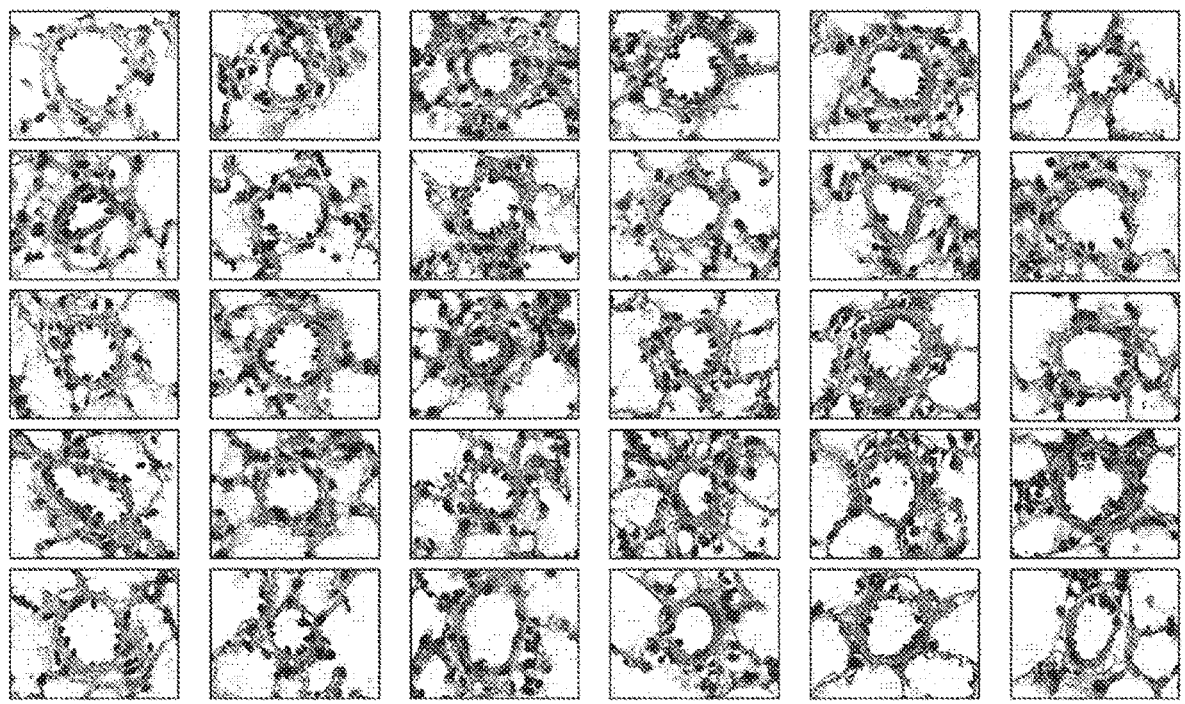
FIG. 11 is a diagram showing the result of H&E staining of a heart excised from the experimental group in which 6 μg of chaetocin is administered to a rat, in which pulmonary arterial hypertension is induced by administering MCT.

The present invention provides a pharmaceutical composition for preventing or treating pulmonary arterial hypertension, comprising an epidithiodioxopiperazine compound represented by the following Formula 1 or a derivative thereof, a natural product-derived epidithiodioxopiperazine derivative, or a pharmaceutically acceptable salt thereof, which has an intramolecular disulfide bond in an epidithiodioxopiperazine ring.

The present invention is based on the discovery that a series of natural or synthetic small molecule compounds having an intramolecular disulfide bond in an epidithiodioxopiperazine ring exerts an effect of treating pulmonary arterial hypertension through the intramolecular disulfide bond included therein. Specifically, the present inventors have found that 5,7-dimethyl-2,3-dithia-5,7-diazabicyclo[2.2.2]octane-6,8-dione, which is a small molecule epidithiodioxopiperazine derivative synthesized to identify chaetocin, which is a representative natural product-derived epidithiodioxopiperazine derivative, and a key mechanism of action, all showed an excellent therapeutic effect on pulmonary arterial hypertension; whereas, the present inventors have also found that a reduced derivative, which similarly includes a dioxopiperazine ring and has two thiol groups instead of the intramolecular disulfide bond, does not exhibit a therapeutic effect on pulmonary arterial hypertension. Therefore, it is obvious that an epidithiodioxopiperazine derivative including an intramolecular disulfide bond can exert an effect of treating pulmonary arterial hypertension regardless of its size or type of substituent. The pulmonary arterial hypertension is a type of hypertension that affects the artery in the lungs and the right side of the heart, and is defined when the mean pulmonary artery pressure at rest is 25 mmHg or greater or when the mean pulmonary artery pressure during exercise is 30 mmHg.

In one form of pulmonary arterial hypertension, small arteries (i.e., pulmonary arteries) and capillaries in the lungs may become narrow, clogged, or damaged, which makes blood flow through the lung harder and increases the pressure inside the pulmonary artery. As a result of the increased pressure, it makes it difficult for the lower right chamber (right ventricle) to pump the blood through the lung, eventually weakening the heart muscles to cause the loss of its function.

Other forms of pulmonary arterial hypertension can continuously be exacerbated, and may sometimes be fatal and serious conditions. Even if some form of pulmonary arterial hypertension cannot be recovered completely, the treatment therefor may help alleviate its symptoms and improve quality of life.

Drugs for specifically treating the pulmonary arterial hypertension have not yet been discovered, and thus conventional vasodilators such as short-acting vasodilators or calcium channel blockers are used for the drug therapy for the pulmonary arterial hypertension. However, cases in which patients respond significantly to short-acting vasodilators are very few, less than about 10% of patients with diagnosis, and there are also cases where patients do not respond to calcium channel blockers. In addition, even if the responses occur, administration is limited due to the numerous side effects of the drugs. Accordingly, pulmonary arterial hypertension differs from general vascular diseases in its treatment mechanism, so that the types of drugs that can be applied are very limited. Further, drugs that have an effect on vascular diseases cannot be expected to have a therapeutic effect on pulmonary arterial hypertension.

For example, the epidithiodioxopiperazine derivative of the present invention may include a natural product-derived compound represented by the following Formulas 2 to 17:

[Formula 2]

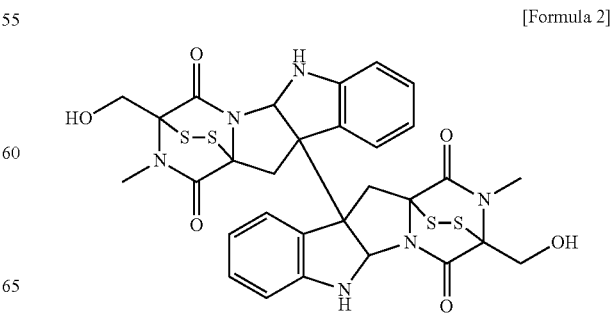

[Formula 3]
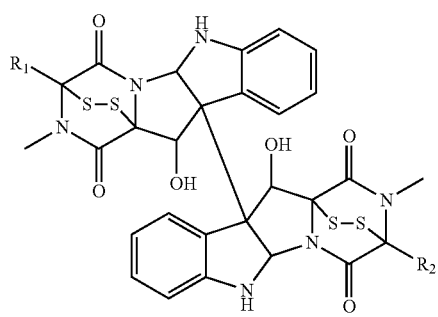
[Formula 4]
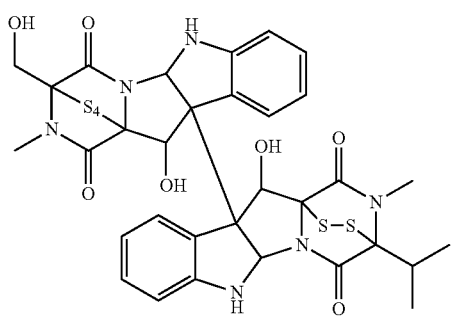
[Formula 5]
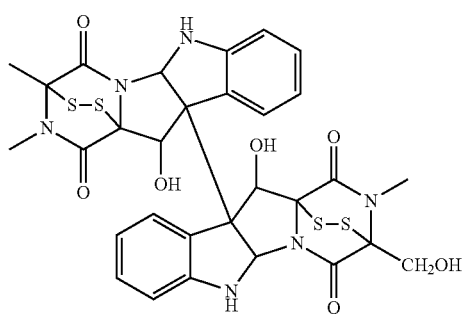
[Formula 6]
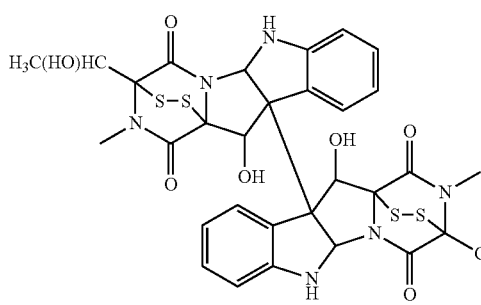
[Formula 7]
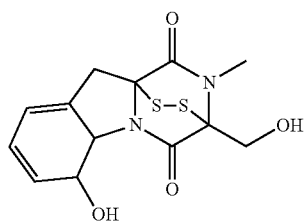
[Formula 8]
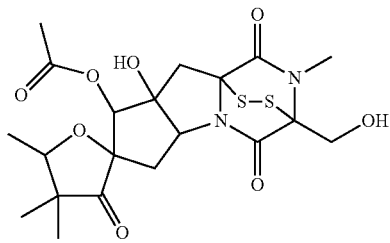
[Formula 9]
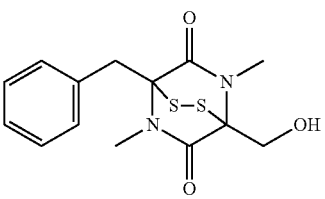
[Formula 10]
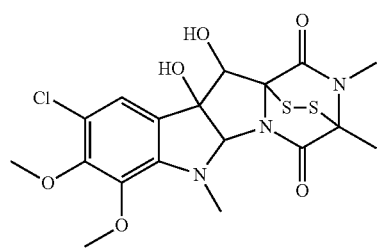
[Formula 11]
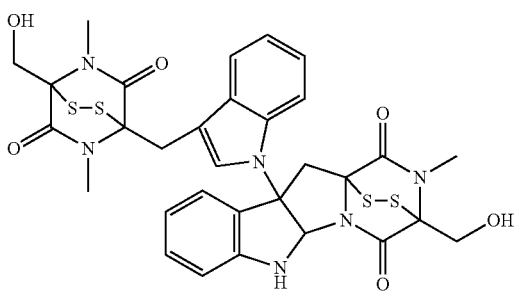
[Formula 12]
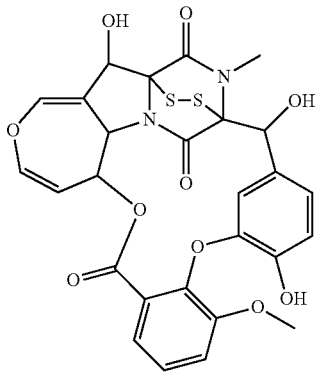

-continued

[Formula 13]
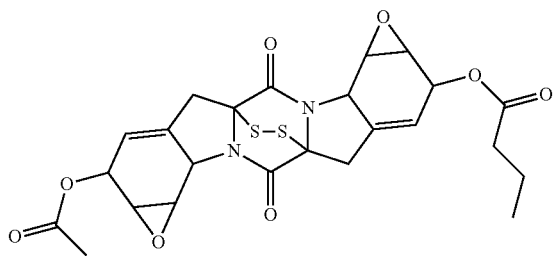

[Formula 14]
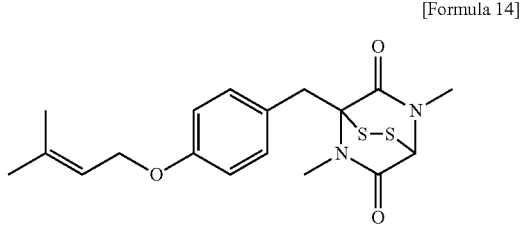

[Formula 15]
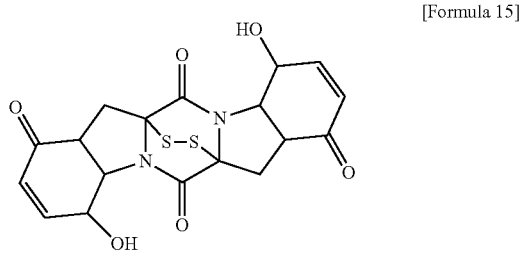

[Formula 16]
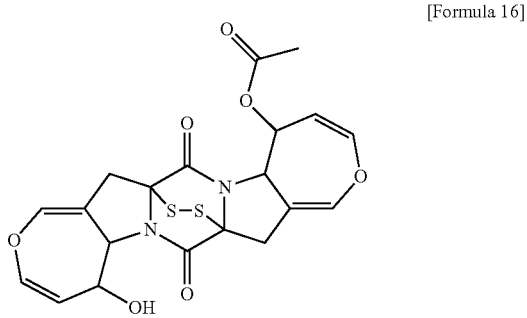

[Formula 17]
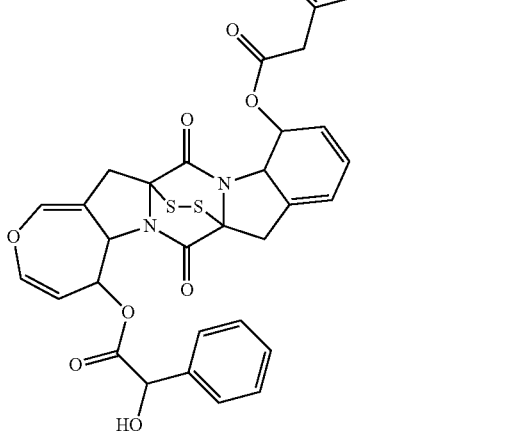

For example, the compound of Formula 2 is an ETP compound called chaetocin, and may be separated from *Chaetomium* spp. [Sekita et al., 1981, *Can. J. Microbiol.*, 27: 766-772].

The compounds of Formula 3 are ETP compounds called verticillins, and may be separated from *Verticillium* spp. or *Penicillium* sp. [Byeng et al., 1999, *Nat. Prod. Lett.*, 13: 213-222; Joshi et al., 1999, *J. Nat. Prod.*, 62: 730-733; Kirby and Robins, 1980, *The Biosynthesis of Mycotoxins*, New York: Sekita et al., 1981, *Can. J. Microbiol.*, 27: 766-772].

The compound of Formula 4 is an ETP compound called leptosin, and may be separated from *Leptosphaetia* sp. [Takahashi et al., 1994, *J. Antibiot.*, 47: 1242-1249].

The compound of Formula 5 is an ETP compound called a verticillin, and may be separated from *Verticillium* spp. [Byeng et al., 1999, *Nat. Prod. Lett.*, 13: 213-222; Joshi et al., 1999, *J. Nat. Prod.*, 62: 730-733; Kirby and Robins, 1980, *The Biosynthesis of Mycotoxins*, New York: Sekita et al., 1981, *Can. J. Microbiol.*, 27: 766-772].

The compound of Formula 6 may be separated from *Gliocladium catenulatum* [Byeng et al., 1999, *Nat. Prod. Lett.*, 13: 213-222; Joshi et al., 1999, *J. Nat. Prod.*, 62: 730-733; Kirby and Robins, 1980, *The Biosynthesis of Mycotoxins*, New York: Sekita et al., 1981, *Can. J. Microbiol.*, 27: 766-772].

The compound of Formula 7 is a representative ETP compound called gliotoxin (GT), and may be separated from bacteria such as *Aspergillus fumigatus*, *Trichoderma vixens*, *Penicillium* spp., or *Candida albicans*, a culture medium thereof, or metabolites or secondary metabolites thereof [Kirby and Robins, 1980, *The Biosynthesis of Mycotoxins*, New York: Academic Press; Shah and Larsen, 1991, *Mycopathologia*, 116: 203-208].

The compound of Formula 8 is an ETP compound called sirodesmin, and may be separated from bacteria such as *Leptosphaeria maculans* or *Sirodesmium diversum*, a culture medium thereof, or metabolites or secondary metabolites thereof [Curtis et al., 1977, *J. Chem. Soc. Perkin Trans.* 1, 180-189; Ferezou et al., 1977, *Nouv. J. Chim.*, 1: 327-334].

The compound of Formula 9 is an ETP compound called hyalodendrin, and may be separated from bacteria such as *Hyalodendron* sp., a culture medium thereof, or metabolites or secondary metabolites thereof [Stillwell et al., 1974, *Can. J. Microbiol.*, 20: 759-764].

The compound of Formula 10 is an ETP compound called sporidesmin A, and may be separated from bacteria such as *Pithomyces chartarum*, a culture medium thereof, or metabolites or secondary metabolites thereof [Kirby and Robins, 1980, *The Biosynthesis of Mycotoxins*, New York: Academic Press].

The compound of Formula 11 is an ETP compound called chetomin, and may be separated from *Chaetomium globosum* [Sekita et al., 1981, *Can. J. Microbiol.*, 27: 766-772].

The compound of Formula 12 is an ETP compound called emestrin, and may be separated from *Aspergillus* spp. [Seya et al., 1986, *Chem. Pharm. Bull.*, 34: 2411-2416].

The compound of Formula 13 is an ETP compound called scabrosin, and may be separated from *Xanthoparmelia scabrosa* [Ernst-Russell et al., 1999, *Aust. J. Chem.*, 52: 279-283; Moerman et al., 2003, *Toxicol. Appl. Pharmacol.*, 190: 232-240].

The compound of Formula 14 is an ETP compound called dithiosilvatin, and may be separated from *Aspergillus silvaticus* [Kawahara et al., 1987, *J. Chem. Soc. Perkin Trans.* 1, 2099-2101].

The compound of Formula 15 is an ETP compound called epicorazine, and may be separated from *Stereum hirsutum*,

*Epicoccum purpurascens*, or *Epicoccum nigrum* [Deffieux et al., 1977, *Acta Christallogr.*, B33: 1474-1478; Kleinwachter et al., 2001, *J. Antibiot.*, 54: 521-525].

The compound of Formula 16 is an ETP compound called aranotin, and may be separated from *Arachniotus aureus* or *Aspergillus terreus* [Neuss et al., 1968, *Antimicrob. Agents Chemother.*, 8: 213-219].

The compound of Formula 17 is an ETP compound called emethallicin, and may be separated from *Aspergillus heterothallicus* [Kawahara et al., 1989, *Chem. Pharm. Bull.*, 37: 2592-2595].

Specifically, the natural product-derived epidithiodioxopiperazine derivative of the present invention may be a compound represented by Formulas 2 to 6, but is not limited thereto.

In an exemplary embodiment of the present invention, the effect of chaetocin (Formula 2), which is a representative natural product-derived epidithiodioxopiperazine derivative including an intramolecular disulfide bond, for treating pulmonary arterial hypertension was confirmed. Specifically, it was confirmed that when chaetocin was administered to experimental animals, in which pulmonary arterial hypertension had been induced by administering monocrotaline, the remarkable hypertrophy of the right ventricle and pulmonary artery intimal thickening, which are shown in a pulmonary arterial hypertension model, were reduced to a level similar to normal. This result is an effect achieved through the intramolecular disulfide bond, and therefore, it is apparent to those skilled in the art that the compounds of Formulas 3 to 6, which include the intramolecular disulfide bond and have a chemical structure similar to that of the chaetocin, will also have an equivalent effect.

The derivative of the epidithiodioxopiperazine compound refers to a compound including an epidithiodioxopiperazine ring, that is, the structural nucleus showing an activity. The derivative may include a compound in which the NH group or the CH group in the ring of the compound represented by Formula 18 is substituted with various substituents known in the art, or a compound having a structure that combines various compounds that are obvious to those skilled in the art, but the derivative is not limited thereto. The modification and substitution of the structure of the compound of Formula 18 can be easily carried out by those skilled in the art, for example, as follows:

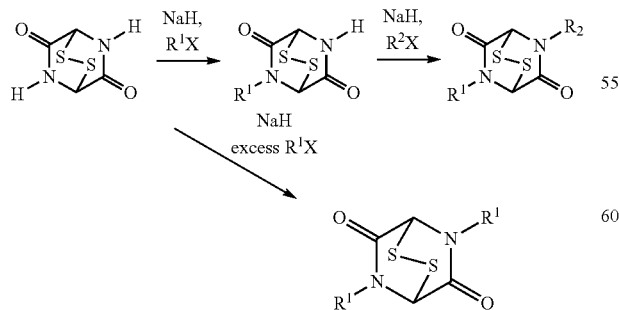

Specifically, the epidithiodioxopiperazine compound and derivative thereof of the present invention are as follows:

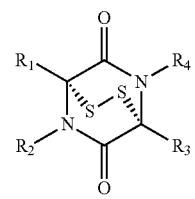

[Formula 1]

wherein, in Formula 1 above, $R_1$ to $R_4$ are each independently hydrogen, linear or branched C1 to C6 alkyl, alkenyl or alkynyl, linear or branched C1 to C6 alkoxy, linear or branched C1 to C6 hydroxyalkyl, substituted or unsubstituted benzyl, linear or branched C1 to C6 alkylaryl, or a substituted or unsubstituted aryl group, and the alkyl may include an oxygen atom in the middle of the chain.

Specifically, $R_1$ to $R_4$ may each independently be hydrogen, methyl, butyl, propenyl, allyl, methoxybenzyl, methoxypropyl, or benzhydryl, but are not limited thereto.

For example, the epidithiodioxopiperazine compound and derivative thereof may be any one of compounds represented by the following Formulas 18 to 26:

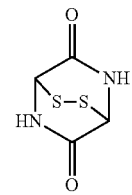

[Formula 18]

[Formula 19]

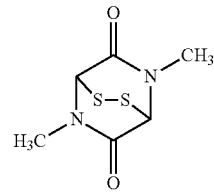

[Formula 20]

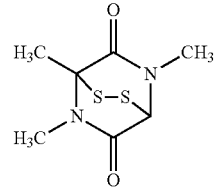

[Formula 21]

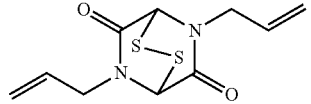

[Formula 22]

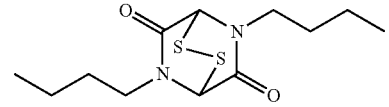

[Formula 23]

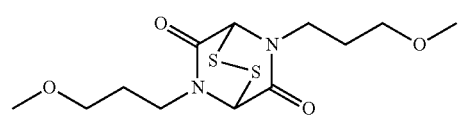

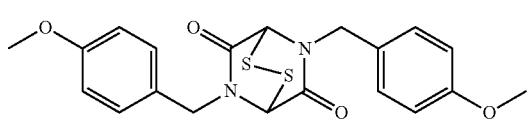
[Formula 24]

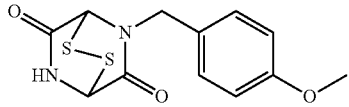
[Formula 25]

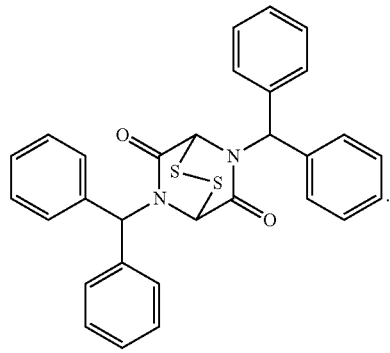
[Formula 26]

More specifically, in Formula 1 above, $R_1$ to $R_4$ are each independently hydrogen, linear or branched C1 to C6 alkyl, alkenyl or alkynyl, or linear or branched C1 to C6 alkoxy, and the alkyl may include an oxygen atom in the middle of the chain.

$R_1$ to $R_4$ may each independently be hydrogen, methyl, butyl, propenyl, allyl, or methoxypropyl, but are not limited thereto.

For example, the epidithiodioxopiperazine compound and derivative thereof may be any one of compounds represented by the following Formulas 18 to 23:

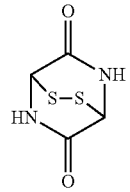
[Formula 18]

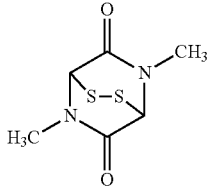
[Formula 19]

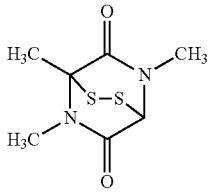
[Formula 20]

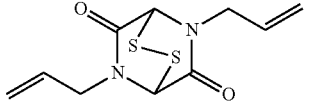
[Formula 21]

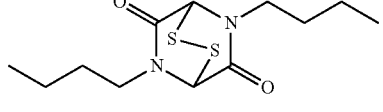
[Formula 22]

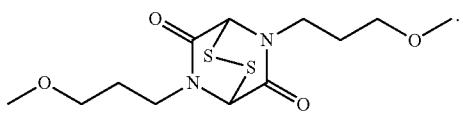
[Formula 23]

The compounds represented by Formulas 18 to 26 can be synthesized and used by those skilled in the art by referring to known methods. As a specific synthesis method, reference can be made to the method disclosed in Korean Patent No. 1633975.

In an exemplary embodiment of the present invention, among a series of epidithiodioxopiperazine derivatives synthesized as described above, which include an intramolecular disulfide bond, 5,7-dimethyl-2,3-dithia-5,7-diazabicyclo[2.2.2]octane-6,8-dione (Formula 19) was confirmed to have an effect of treating pulmonary arterial hypertension. Specifically, it was confirmed that when the compound of Formula 19 was administered to experimental animals, in which pulmonary arterial hypertension had been induced by administering monocrotaline, similar to natural product-derived chaetocin, the remarkable hypertrophy of the right ventricle and pulmonary artery intimal thickening, which are shown in a pulmonary arterial hypertension model, were reduced to a level similar to normal. This result is an effect achieved through the intramolecular disulfide bond, and therefore, it is apparent to those skilled in the art that the compounds of Formulas 18 to 23, which include the intramolecular disulfide bond, share the same structural nucleus as the compound of Formula 19, and in which only the nitrogen and/or carbon atoms on the ring are substituted with substituents having a similar property, will also have an equivalent effect.

The epidithiodioxopiperazine compound or derivatives thereof may be separated from natural sources, acquired from natural sources and then prepared by chemical reforming, or prepared from chemical synthesis by those skilled in the art referencing known preparation methods. Preferably, the epidithiodioxopiperazine compound or derivatives thereof may be used by being separated from bacteria, a culture medium thereof, or metabolites according to known methods in the art, or prepared from syntheses using methods described in the prior patent of the present invention (Korean Patent No. 1633975).

The composition of the present invention can achieve an effect of preventing or treating pulmonary arterial hypertension through the intramolecular disulfide bond. For example, the effect of preventing or treating pulmonary arterial hypertension can be achieved by mimicking an intracellular PrxII activity, but the specific mechanism of action is not limited thereto.

The epidithiodioxopiperazine compound or derivative thereof of the present invention may be used in the form of a pharmaceutically acceptable salt. In addition, the compound or derivative thereof of the present invention may be used alone or in combination with other pharmaceutically acceptable compounds.

The term "pharmaceutically acceptable salt" used in the present invention means all salts having target biological and/or physiological activities of the compound or derivatives, and minimally exhibiting undesirable toxicological effects. In the present invention, the type of the salt is not limited as long as the salt maintains a diketopiperazine ring including an intramolecular disulfide bridge. As the salt, an acid addition salt formed by a pharmaceutically acceptable free acid is useful. The acid addition salt may be prepared using common methods such as dissolving a compound in an excess aqueous solution, and precipitating this salt using a water-miscible organic solvent such as methanol, ethanol, acetone, or acetonitrile. An equimolar compound, and an acid or alcohol in water (for example, glycol monomethyl ether) are heated, and then the mixture may be dried by evaporation, or the precipitated salt may be suction filtered. Herein, an inorganic acid or an organic acid may be used as the free acid, and hydrochloric acid, hydrobromic acid, phosphoric acid, nitric acid, sulfuric acid, stannic acid, and the like may be used as the inorganic acid, and methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like may be used as the organic acid; however, the inorganic acid and the organic acid are not limited thereto.

In addition, a pharmaceutically acceptable metal salt may be prepared using a base. An alkali metal or alkaline earth metal salt is obtained by, for example, dissolving a compound in an excess alkali metal hydroxide or alkaline earth metal hydroxide solution, filtering the non-soluble compound salt, drying the filtrate, and drying the result. Herein, preparing a sodium, potassium, or calcium salt as the metal salt is pharmaceutically suitable, but the metal salt is not limited thereto. Furthermore, a corresponding silver salt may be obtained by reacting the alkali metal or alkaline earth metal salt with a suitable silver salt (for example, silver nitrate).

The pharmaceutically acceptable salt of the epidithiodioxopiperazine compound or derivatives thereof according to the present invention includes, unless otherwise specified, all salts of acidic or basic groups that can exist. For example, the pharmaceutically acceptable salt may include sodium, calcium, and potassium salts of a hydroxyl group, and as other pharmaceutically acceptable salts of an amino group, hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate) salts, and the like may be included, and these may be prepared using preparation methods of salts known in the art.

The composition according to the present invention may further include proper carriers, diluting agents, and diluents commonly used for the preparation of pharmaceutical compositions. The composition is sterilized or aseptic, may be water, a buffer, an isotonic agent, and the like, and the solution is sterilized or aseptic, or may include other ingredients known to those skilled in the art, which do not cause allergies or other harmful reactions when applied to animals or humans.

The term "pharmaceutically acceptable carrier" used in the present invention includes all random solvents, dispersive media, coating materials, antimicrobial agents, antifungal agents, isotonic agents, and the like. Using the media and the formulations as pharmaceutically active materials is well known in the related art. In addition to common media or formulations non-miscible with active ingredients, the use of the media and the formulations described above is considered in therapeutic compositions. In addition, supplementary active ingredients may be mixed with the composition described above.

The composition may be prepared as formulations such as liquids, emulsions, suspensions, or creams, or may be used for non-oral administration. The amount of the composition used may be an amount commonly used for preventing vascular restenosis, and is preferably different depending on the age, gender, and condition of patients, in vivo absorbance of active substances, inactivation rate, and drugs used in combination.

Additionally, the present invention provides a method for preventing or treating pulmonary arterial hypertension, comprising administering the pharmaceutical composition to a subject in need thereof.

In the present invention, the term "prevention" means all actions that suppress pulmonary arterial hypertension or delay the outbreak of the diseases by the administration of the pharmaceutical composition, and the term "treatment" means all actions that enable the symptoms of pulmonary arterial hypertension to improve or change for the better by the administration of the pharmaceutical composition.

In the present invention, the term "subject" means all animals including human beings which have developed or have a possibility of developing pulmonary arterial hypertension, and the pulmonary arterial hypertension may be effectively prevented or treated by administering the pharmaceutical composition of the present invention into an entity. In addition, the pharmaceutical composition of the present invention may be administered in combination with known therapeutic agents for pulmonary arterial hypertension.

The pharmaceutical composition of the present invention is administered with a therapeutically effective dose. The term "therapeutically effective dose" means an amount sufficient to treat diseases in a reasonable benefit/risk ratio applicable to medical treatments and not to cause side effects, and the level of the effective dose may be readily determined by those skilled in the art depending on the factors including the gender, age, weight, and health condition of patients, severity of the disease, the activity of drugs, the sensitivity to drugs, administration methods, administration time, administration paths and excretion rates, treatment period, drugs mixed or simultaneously used, and other factors well known in the field of medicine.

The term "administration" in the present invention means introducing a prescribed material to a patient using proper methods, and the composition may be administered via any general path as long as the composition reaches a target tissue. Although not limited thereto, the administration method is preferably non-oral administration, and more preferably, local administration to lesions. For local administration of drugs, double balloon catheters, dispatches or microporous balloons, and the like may be used, and particularly, stents or sustained microparticles may be used for long-term drug delivery. Most preferably, the composition of the present invention may be directly administered to the area of occurrence of pulmonary arterial hypertension by applying the composition inside a stent.

In addition, the present invention provides a drug delivery device for local administration including the pharmaceutical composition for preventing or treating pulmonary arterial hypertension. The drug delivery device for local administration may include double balloon catheters, dispatches, microporous balloons, stents, and the like, but is not limited thereto, and is preferably a stent.

The term "stent" in the present invention means a general device for endoluminal application as described above such as intravascular application, and means a cylindrical medical material normalizing a blood flow by being inserted to a narrowed or clogged vascular area under fluoroscopy without surgical laparotomy when the blood flow is disabled due to the development of diseases at a location to have a smooth blood flow. For example, a vascular stent is described in "Textbook of Interventional Cardiology" (Saunders Company, 1994) written by Eric J. Topol. Preferably, the stent is a sustained drug-releasing stent.

As the method of coating the pharmaceutical composition of the present invention onto the stent, common coating methods known to those skilled in the art may be applied, and examples thereof include a dip-coating method and a polymer-coating method, the dip-coating method is the simplest coating method, and biological effects of the drug itself are readily observed since only the pharmaceutical composition is coated; however, the method is not limited thereto. Preferably, the stent of the present invention may be prepared by coating the composition on a drug-releasing stent after being mixed with a polymer material so that the composition according to the present invention is slowly released. The polymer material that can be used as a drug-releasing stent is widely known in the art, and examples thereof include polyurethane, polyethylene terephthalate, PLLA-poly-glycolic acid copolymer (PLGA), polycaprolactone, poly-(hydroxybutyrate/hydroxyvalerate) copolymer, polyvinylpyrrolidone, polytetrafluoroethylene, poly(2-hydroxyethylmethacrylate), poly(ether urethane urea), silicone, acryl, epoxide, polyester, urethane, pyrene, a polyphosphazine polymer, a fluoro polymer, polyamide, polyolefin, and a mixture thereof, but are not limited thereto.

The stent may be formed with one or more materials selected from the group consisting of polysaccharide, heparin, gelatin, collagen, alginate, hyaluronic acid, alginic acid, carrageenan, chondroitin, pectin, chitosan, and derivatives and copolymers thereof, or may be further coated with an antithrombotic layer including these. These materials may be properly combined to a biocompatible topcoat as described in US Patent Application Laid-Open Publication No. US 2006/0083772. The method for forming a stent from the mixture of a polymer and a drug compound is disclosed in Blindt et al., 1999, *Int. J. Artif. Organs*, 22: 843-853.

MODE FOR CARRYING OUT THE INVENTION

Hereinbelow, the present invention will be described in detail with accompanying exemplary embodiments. However, the exemplary embodiments disclosed herein are only for illustrative purposes and should not be construed as limiting the scope of the present invention.

Preparation Example 1: Preparation of Monocrotaline-Induced Pulmonary Arterial Hypertension Experimental Animals Male SD rats weighing approximately 210 g were used as animal models. In order to induce pulmonary arterial hypertension, a single intraperitoneal injection of monocrotaline (MCT) at a dose of 60 mg/kg was carried out. Accordingly, the rat models in which pulmonary arterial hypertension is induced were maintained for 3 weeks while test drugs were administered or not administered, and then the rat models were sacrificed. Thereafter, the hearts were excised and analyzed.

Example 1: Therapeutic Effect 1 of Epidithiodioxopiperazine Compounds for Pulmonary Arterial Hypertension Chaetocin (the compound of Formula 2), which is a representative epidithiodioxopiperazine compound, was administered as a test drug to the pulmonary arterial hypertension animal models prepared according to Preparation Example 1 above at each dose of 6 μg, 12 μg, and 30 μg every 3 days. Normal rats in which MCT is not administered were used as the control group; and rats in which pulmonary arterial hypertension is induced by administering only MCT were used as the MCT group. The control group and each experimental group consisted of 3 to 4 rats.

The hearts were excised as in Preparation Example 1, and the excised hearts were measured for their total mass. Thereafter, the right ventricle (RV) was separated and the masses of each of the right ventricle, left ventricle, and cardiac septum (LV+septum) were separately measured to calculate the ratio. The results of the measurement of each experimental animal, the normal rats (control group), the MCT group, and the experimental groups (chaetocin groups; MCT+(dose μg)) in which chaetocin is administered at each dose of 30 μg, 12 μg, and 6 μg are shown in order in Tables 1 to 5.

TABLE 1

|   | Total mass (mg) | RV (mg) | LV + Septum (mg) | RV/LV + Septum |
|---|---|---|---|---|
| 1 | 968 | 212 | 756 | 0.28 |
| 2 | 946 | 212 | 734 | 0.29 |
| 3 | 959 | 214 | 745 | 0.29 |
| 4 | 968 | 207 | 761 | 0.27 |
| Average | 960.3 | 211.3 | 749.0 | 0.28 |

TABLE 2

|   | Total mass (mg) | RV (mg) | LV + Septum (mg) | RV/LV + Septum |
|---|---|---|---|---|
| 1 | 1257 | 383 | 874 | 0.44 |
| 2 | 1423 | 412 | 1008 | 0.41 |
| 3 | 1462 | 438 | 1024 | 0.43 |
| 4 | 1496 | 473 | 1023 | 0.46 |
| Average | 1409.5 | 427.3 | 982.3 | 0.44 |

TABLE 3

|   | Total mass (mg) | RV (mg) | LV + Septum (mg) | RV/LV + Septum |
|---|---|---|---|---|
| 1 | 1185 | 264 | 921 | 0.29 |
| 2 | 865 | 176 | 689 | 0.26 |
| 3 | 1135 | 261 | 874 | 0.30 |
| 4 | 1258 | 259 | 999 | 0.26 |
| Average | 1110.8 | 240.0 | 870.8 | 0.3 |

TABLE 4

| | Total mass (mg) | RV (mg) | LV + Septum (mg) | RV/LV + Septum |
|---|---|---|---|---|
| 1 | 1174 | 261 | 913 | 0.29 |
| 2 | 1263 | 295 | 968 | 0.30 |
| 3 | 1147 | 221 | 926 | 0.24 |
| Average | 1194.7 | 259.0 | 935.7 | 0.28 |

TABLE 5

| | Total mass (mg) | RV (mg) | LV + Septum (mg) | RV/LV + Septum |
|---|---|---|---|---|
| 1 | 922 | 190 | 732 | 0.26 |
| 2 | 856 | 175 | 681 | 0.26 |
| 3 | 947 | 205 | 742 | 0.28 |
| Average | 908.3 | 190.0 | 718.3 | 0.26 |

Further, the sizes of the excised entire hearts and separated right ventricles were visually observed (FIG. 1), and the thicknesses of the pulmonary arterial walls were measured by H&E staining (FIGS. 2 to 11). In addition, in order to visualize the difference in the heart and pulmonary artery according to the dose-dependent chaetocin administration after the pulmonary arterial hypertension induction in the pulmonary arterial hypertension model, the average values of the heart mass, the ratio of the right ventricle to the left ventricle, and the thickness of the pulmonary artery wall, which are calculated from the hearts excised from each animal model, are shown in FIGS. 12 to 14, respectively.

Figure 12:
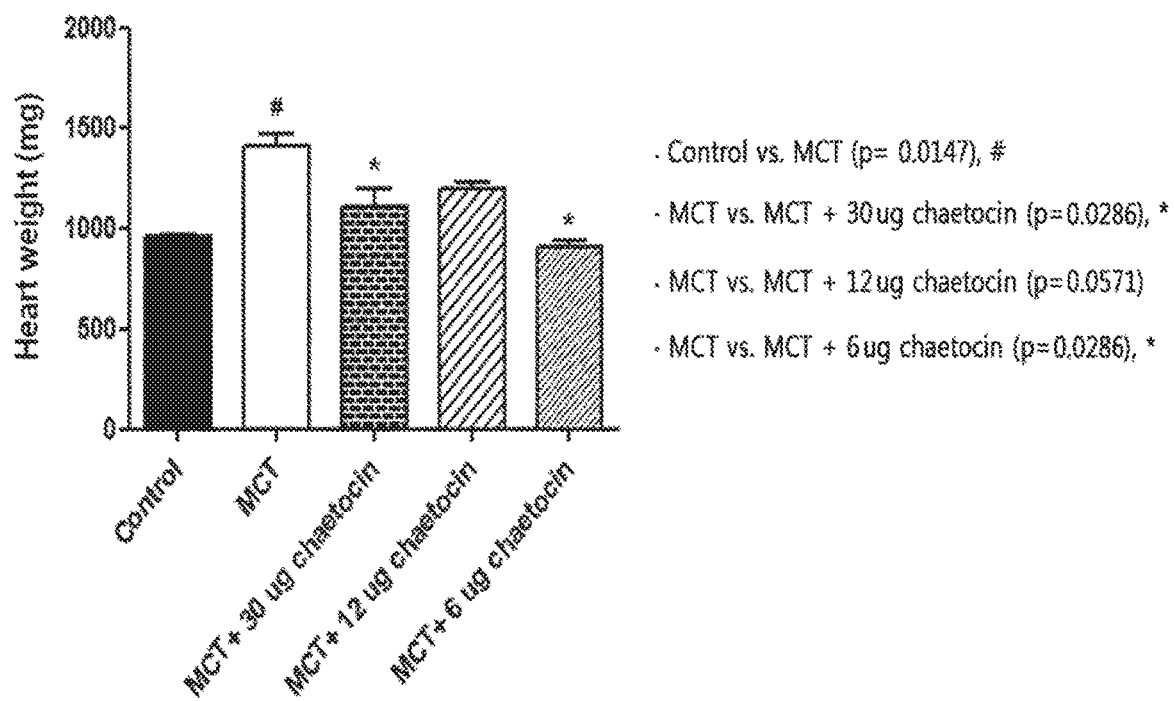
FIG. 12 is a graph comparing the mean total mass of hearts excised from the control group, MCT administration group, and dose-dependent chaetocin administration experimental groups.
Figure 13:
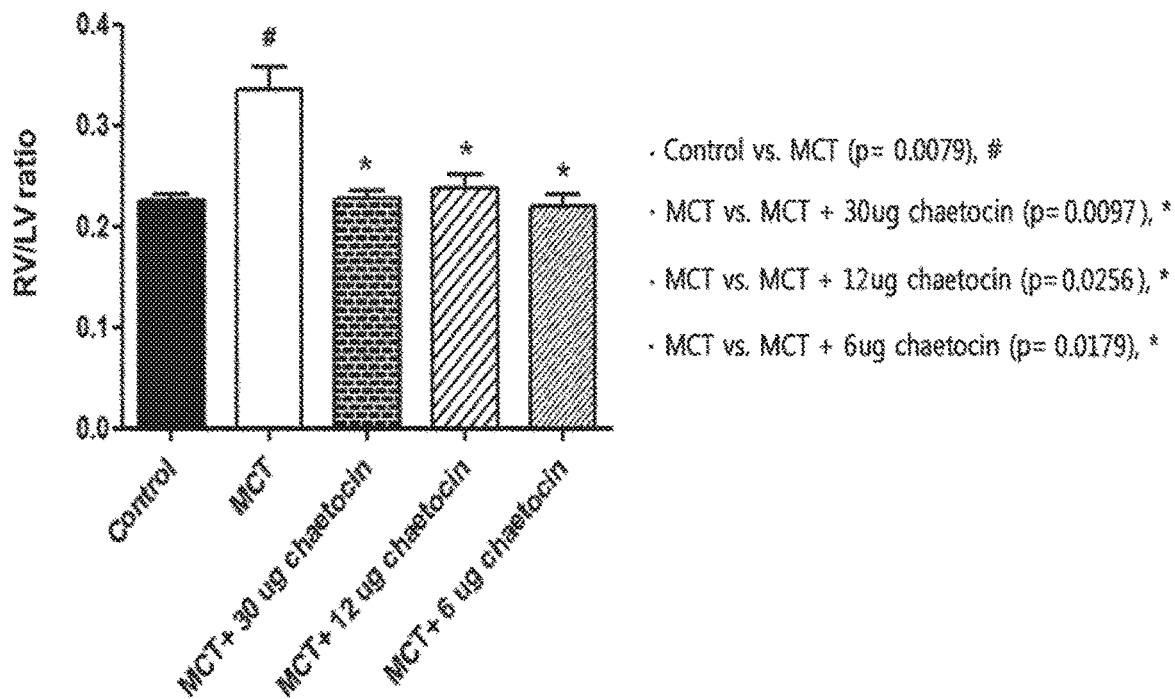
FIG. 13 is a graph comparing the mass ratio of right ventricles over the sum of left ventricles and cardiac septa in hearts excised from the control group, MCT administration group, and dose-dependent chaetocin administration experimental groups.
Figure 14:
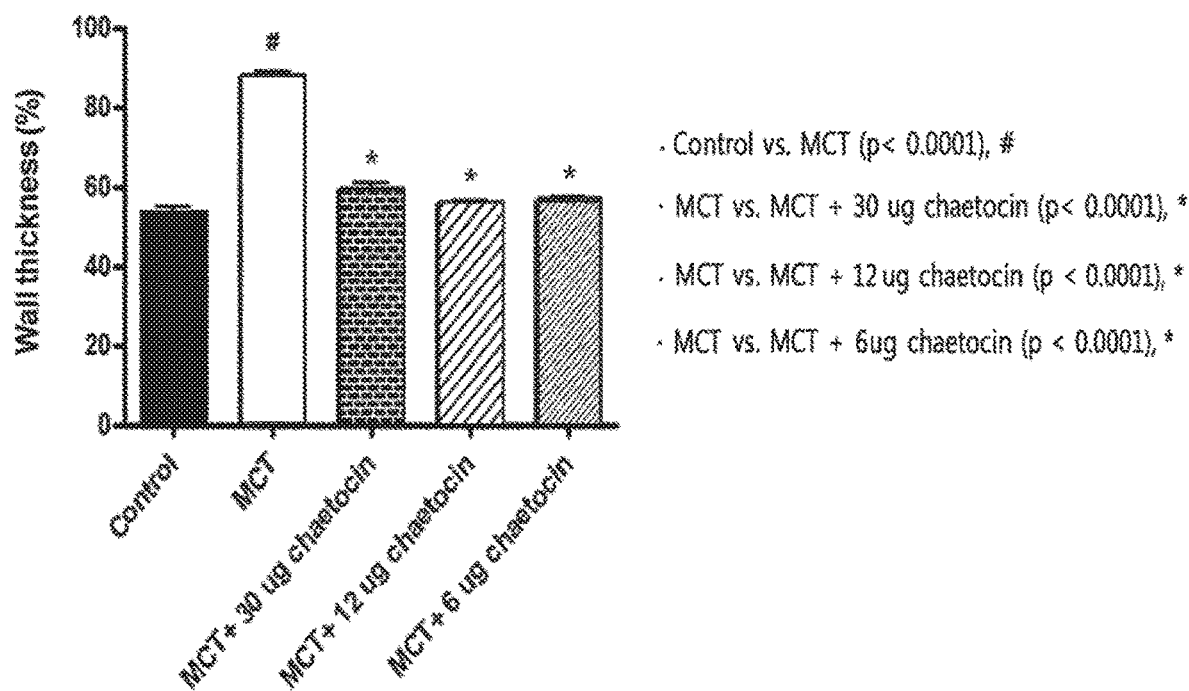
FIG. 14 is a graph comparing the average thickness of pulmonary arterial walls excised from the control group, MCT administration group, and dose-dependent chaetocin administration experimental groups.

As shown in FIGS. 12 to 14, in the groups in which chaetocin is administered, the size of the heart and the thickness of the pulmonary artery wall were similar to those of the control group. This confirms that the chaetocin administration at all doses could efficiently block the hypertrophy of the pulmonary artery wall and the hypertrophy of the heart, especially the right ventricle, by MCT administration.

Example 2: Therapeutic Effect 2 of Epidithiodioxopiperazine Compounds for Pulmonary Arterial Hypertension 5,7-Dimethyl-2,3-dithia-5,7-diazabicyclo[2.2.2]octane-6,8-dione (the compound of Formula 19; marked as A-2 in the Figures), which is another epidithiodioxopiperazine compound, was administered as a test drug to the pulmonary arterial hypertension animal models prepared according to Preparation Example 1 above at each dose of 3 μg and 6 μg every 3 days. As in Example 1, normal rats in which MCT is not administered were used as the control group; and rats in which pulmonary arterial hypertension is induced by administering only MCT were used as the MCT group. The control group and each experimental group consisted of 3 to 4 rats.

Similar to Preparation Example 1, the rats were maintained for 2 weeks, and then the hearts were excised. The excised hearts were measured for their total mass. Thereafter, the right ventricle was separated and the masses of each of the right ventricle, left ventricle, and cardiac septum were separately measured to calculate the ratio.

Figure 15:
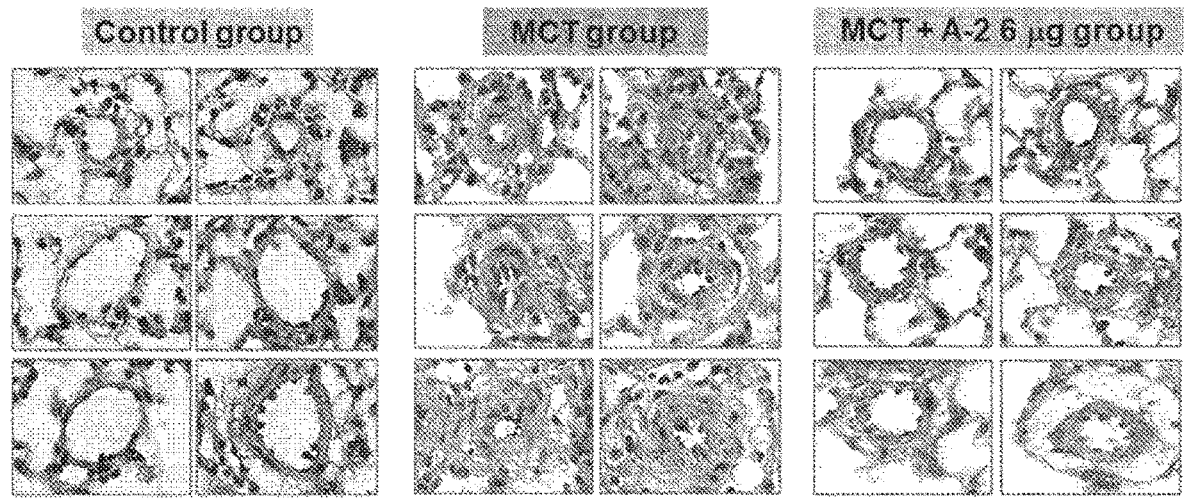
FIG. 15 is an enlarged view showing the results of H&E staining of hearts excised from the control group, MCT administration group, and 5,7-dimethyl-2,3-dithia-5,7-diazabicyclo[2.2.2]octane-6,8-dione administration experimental group.

Further, pulmonary artery walls were observed from the excised hearts through H&E staining, and the results thereof are shown in FIG. 15. In addition, in order to visualize the difference in the heart and pulmonary artery according to the dose-dependent 5,7-dimethyl-2,3-dithia-5,7-diazabicyclo[2.2.2]octane-6,8-dione administration after the pulmonary arterial hypertension induction in the pulmonary arterial hypertension model, the average values of the ratio of the right ventricle to the left ventricle and the thickness of the pulmonary artery wall, which are calculated from the heart excised from each animal model, are shown in FIGS. 16 and 17, respectively.

Figure 16:
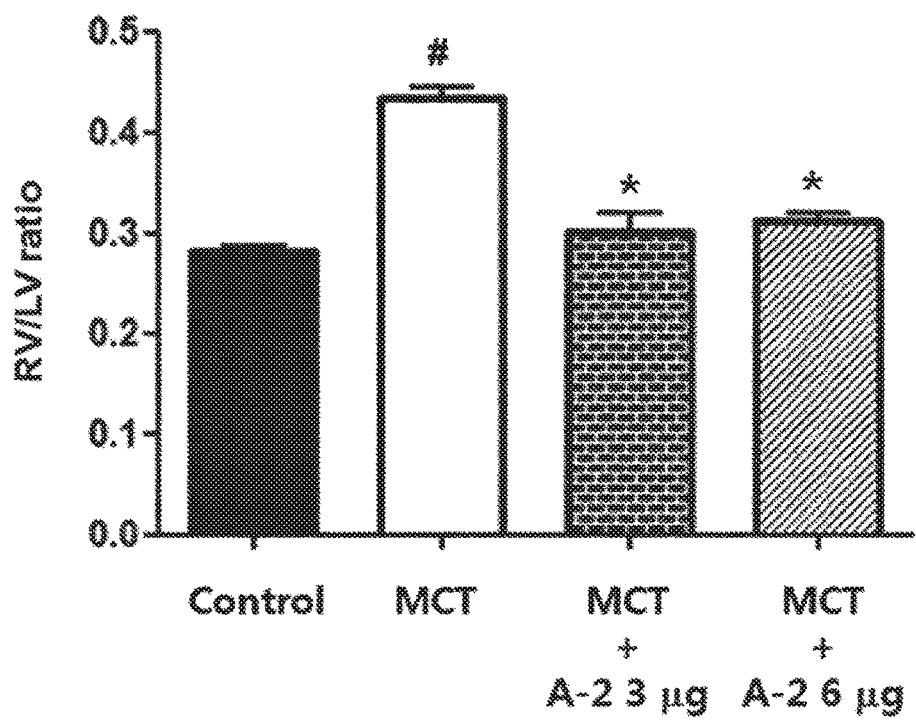
FIG. 16 is a graph comparing the mass ratio of right ventricles over the sum of left ventricles and cardiac septa in hearts excised from the control group, MCT administration group, and dose-dependent 5,7-dimethyl-2,3-dithia-5,7-diazabicyclo[2.2.2]octane-6,8-dione administration experimental groups.
Figure 17:
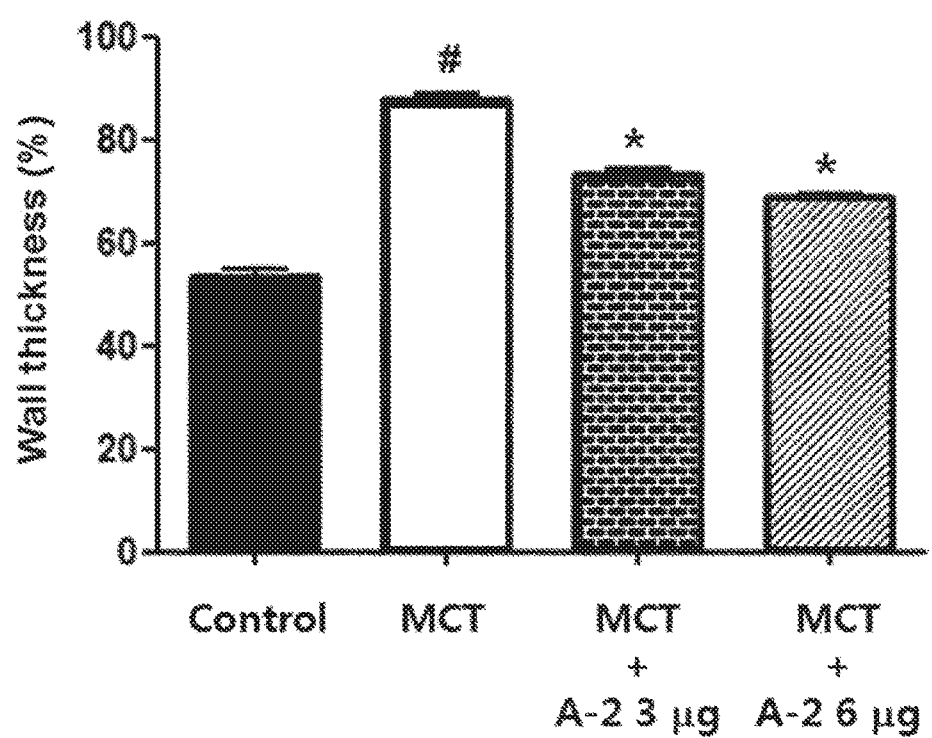
FIG. 17 is a graph comparing the average thickness of pulmonary arterial walls excised from the control group, MCT administration group, and dose-dependent 5,7-dimethyl-2,3-dithia-5,7-diazabicyclo[2.2.2]octane-6,8-dione administration experimental groups.

As shown in FIGS. 16 and 17, in the groups in which 5,7-dimethyl-2,3-dithia-5,7-diazabicyclo[2.2.2]octane-6,8-dione is administered, the size of the heart and the thickness of the pulmonary artery wall were similar to those of the control group. This confirms that the 5,7-dimethyl-2,3-dithia-5,7-diazabicyclo[2.2.2]octane-6,8-dione administration at all doses could efficiently block the hypertrophy of the pulmonary artery wall and the hypertrophy of the heart, especially the right ventricle, by MCT administration.

The invention claimed is:

1. A method for preventing or treating pulmonary arterial hypertension, comprising administering a pharmaceutical composition to a subject in need thereof,
   wherein the pharmaceutical composition comprises an epidithiodioxopiperazine compound represented by the following Formula 1 or a derivative thereof, a natural product-derived epidithiodioxopiperazine derivative, or a pharmaceutically acceptable salt thereof, which has an intramolecular disulfide bond in an epidithiodioxopiperazine ring as an active ingredient,
   wherein the natural produced-derived epidithiodioxopiperazine derivative is any one of compounds represented by the following Formulas 2 to 17:

[Formula 1]
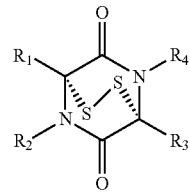

[Formula 2]
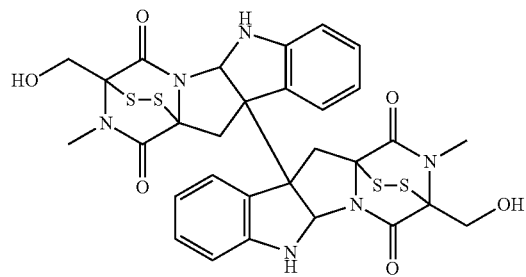

[Formula 3]
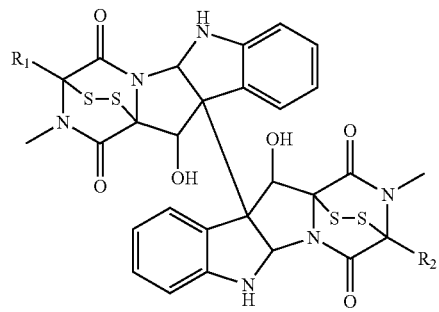

[Formula 4]
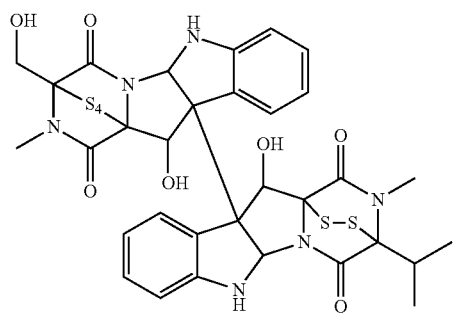
[Formula 5]
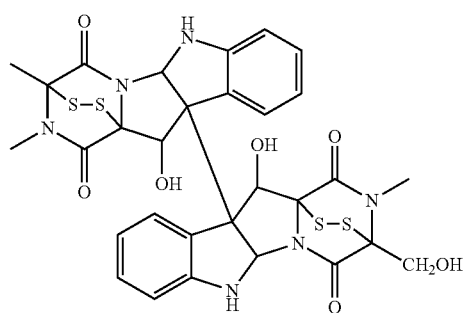
[Formula 6]
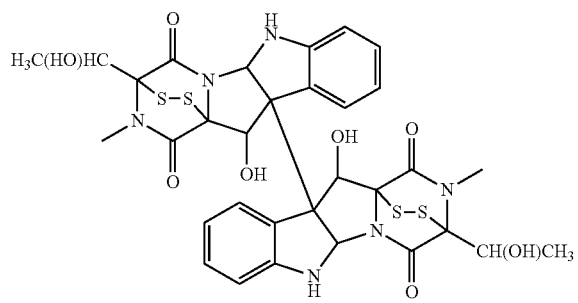
[Formula 7]
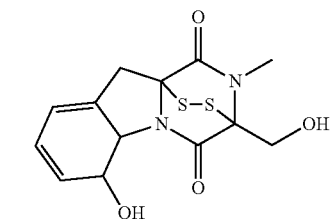
[Formula 8]
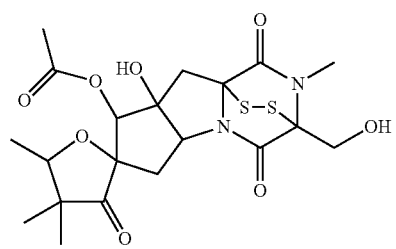
[Formula 9]
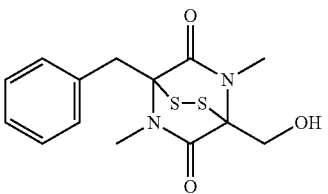
[Formula 10]
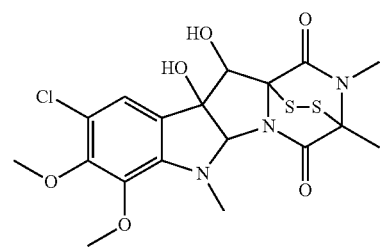
[Formula 11]
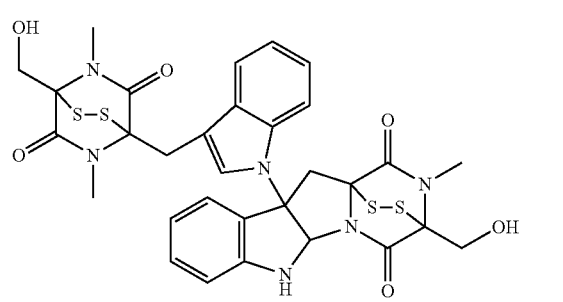
[Formula 12]
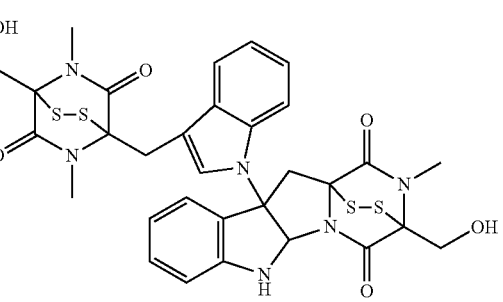
[Formula 13]
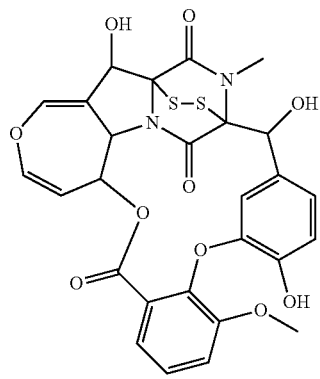
[Formula 14]
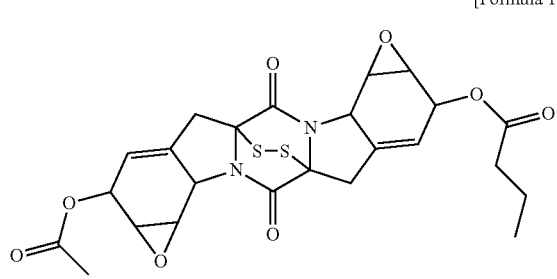

[Formula 15]

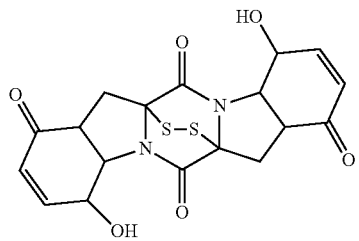

[Formula 2]

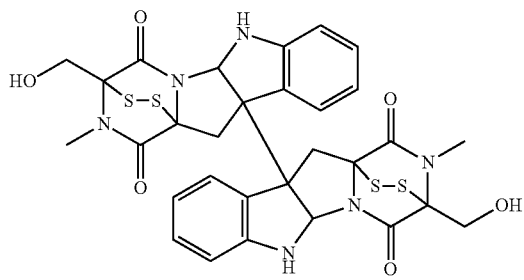

[Formula 16]

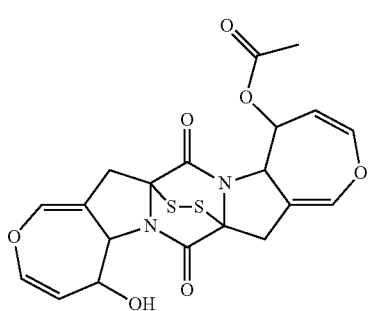

[Formula 3]

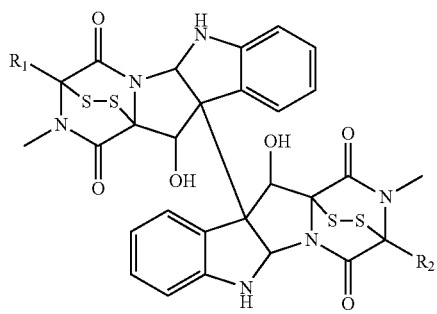

[Formula 4]

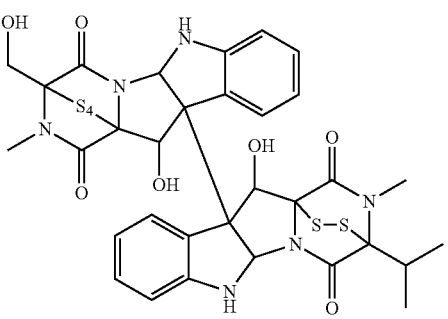

[Formula 17]

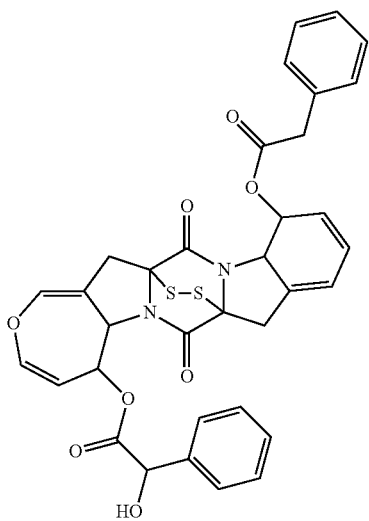

[Formula 5]

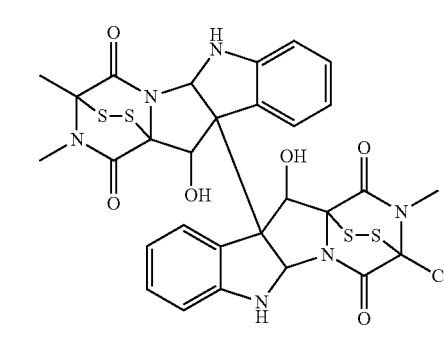

[Formula 6]

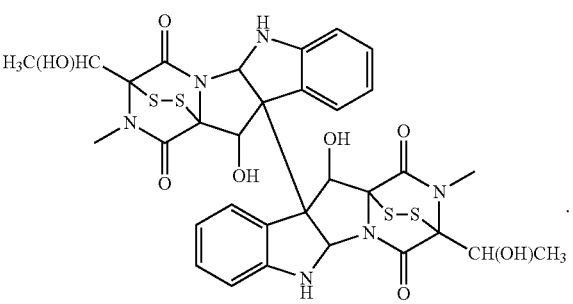

wherein, in Formula 1 above, $R_1$ to $R_4$ are each independently hydrogen, linear or branched C1 to C6 alkyl, alkenyl or alkynyl, linear or branched C1 to C6 alkoxy, linear or branched C1 to C6 hydroxyalkyl, substituted or unsubstituted benzyl, linear or branched C1 to C6 alkylaryl, or a substituted or unsubstituted aryl group, and the alkyl comprises or does not comprise an oxygen atom in the middle of the chain.

2. The method of claim 1, wherein the natural product-derived epidithiodioxopiperazine derivative is any one of compounds represented by the following Formulas 2 to 6:

3. The method of claim 1, wherein $R_1$ to $R_4$ are each independently hydrogen, methyl, butyl, propenyl, allyl, methoxybenzyl, methoxypropyl, or benzhydryl.

4. The method of claim 3, wherein the compound represented by Formula 1 is any one of the following Formulas 18 to 26:

[Formula 18]
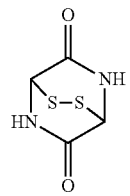

[Formula 19]
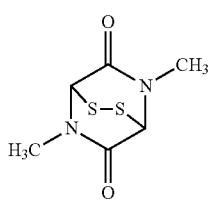

[Formula 20]
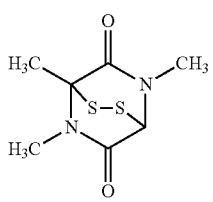

[Formula 21]
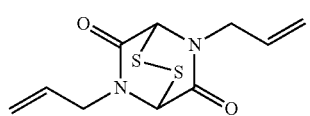

[Formula 22]
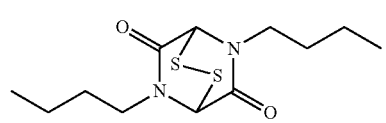

[Formula 23]
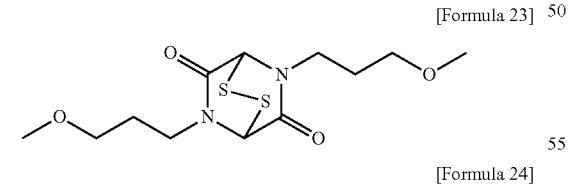

[Formula 24]
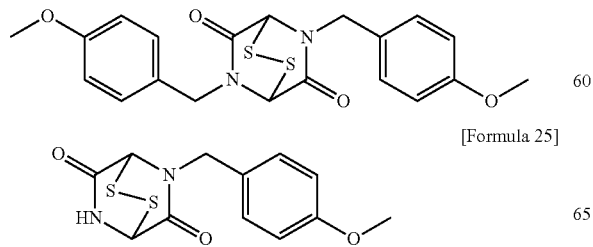

[Formula 25]

[Formula 26]
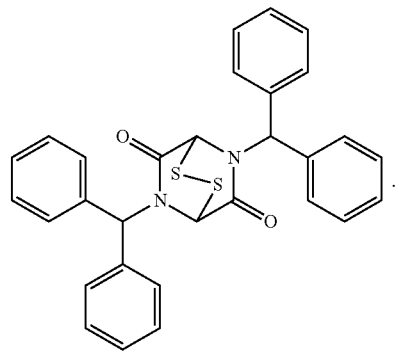

5. The method of claim 1, wherein $R_1$ to $R_4$ are each independently hydrogen, linear or branched C1 to C6 alkyl, alkenyl or alkynyl, or linear or branched C1 to C6 alkoxy,
   and the alkyl comprises or does not comprise an oxygen atom in the middle of the chain.

6. The method of claim 1, wherein $R_1$ to $R_4$ are each independently hydrogen, methyl, butyl, propenyl, allyl, or methoxypropyl.

7. The method of claim 6, wherein the compound represented by Formula 1 is any one of the following Formulas 18 to 23:

[Formula 18]
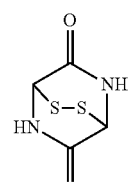

[Formula 19]
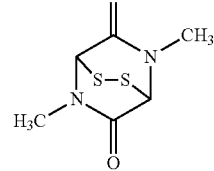

[Formula 20]
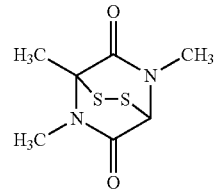

[Formula 21]
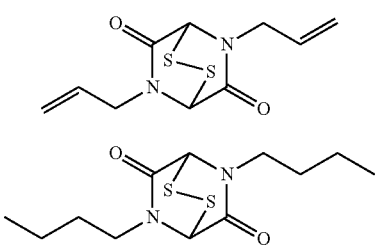

[Formula 22]
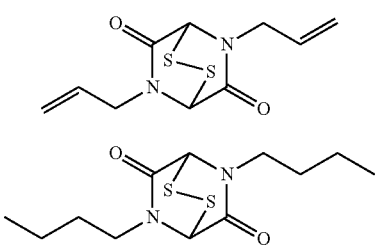

-continued
[Formula 23]
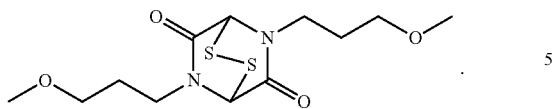
8. The method of claim 1, wherein the prevention or treatment of pulmonary arterial hypertension is achieved by mimicking an intracellular activity of PrxII.
* * * * *